(12) United States Patent
Shekhar et al.

(10) Patent No.: US 6,271,394 B1
(45) Date of Patent: Aug. 7, 2001

(54) PROCESS FOR PRODUCING AMINO ACID AMIDES

(75) Inventors: Ratna Shekhar, Madison; Michael John Girgis, Montville, both of NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/704,500

(22) Filed: Nov. 2, 2000

Related U.S. Application Data (60) Provisional application No. 60/163,424, filed on Nov. 3, 1999.

(51) Int. Cl.$^7$ .................................................. C07D 207/00
(52) U.S. Cl. ............................................. 548/537; 564/134
(58) Field of Search ............................... 548/537; 564/134

(56) References Cited

U.S. PATENT DOCUMENTS

4,017,513    4/1977    Roteman .............................. 548/537

*Primary Examiner*—Fiona T. Powers
(74) *Attorney, Agent, or Firm*—David E. Wildman

(57) ABSTRACT

Disclosed are methods for the synthesis of amino acid amides which comprise providing a fixed bed of a cation exchange resin, admixing a primary alcohol and an amino acid in a reaction vessel in fluid communication with the fixed bed to form a first mixture, contacting the fixed bed of cation exchange resin with the first mixture for a period of time, thereby causing amino acid ester intermediate to be formed on the cation exchange resin, adding liquid ammonia to the reaction vessel, and contacting the fixed bed of cation exchange resin with ammonia, the fixed bed having previously been contacted with the first mixture.

16 Claims, 6 Drawing Sheets

(A) Esterification (B) Amidation

PROCESS FOR PRODUCING AMINO ACID AMIDES

This application claims priority under 35 U.S.C. § 119(e) from provisional application No. 60/163,424, the contents of which is incorporated by reference herein in its entirety.

BACKGROUND OF THE INVENTION

Figure 1:
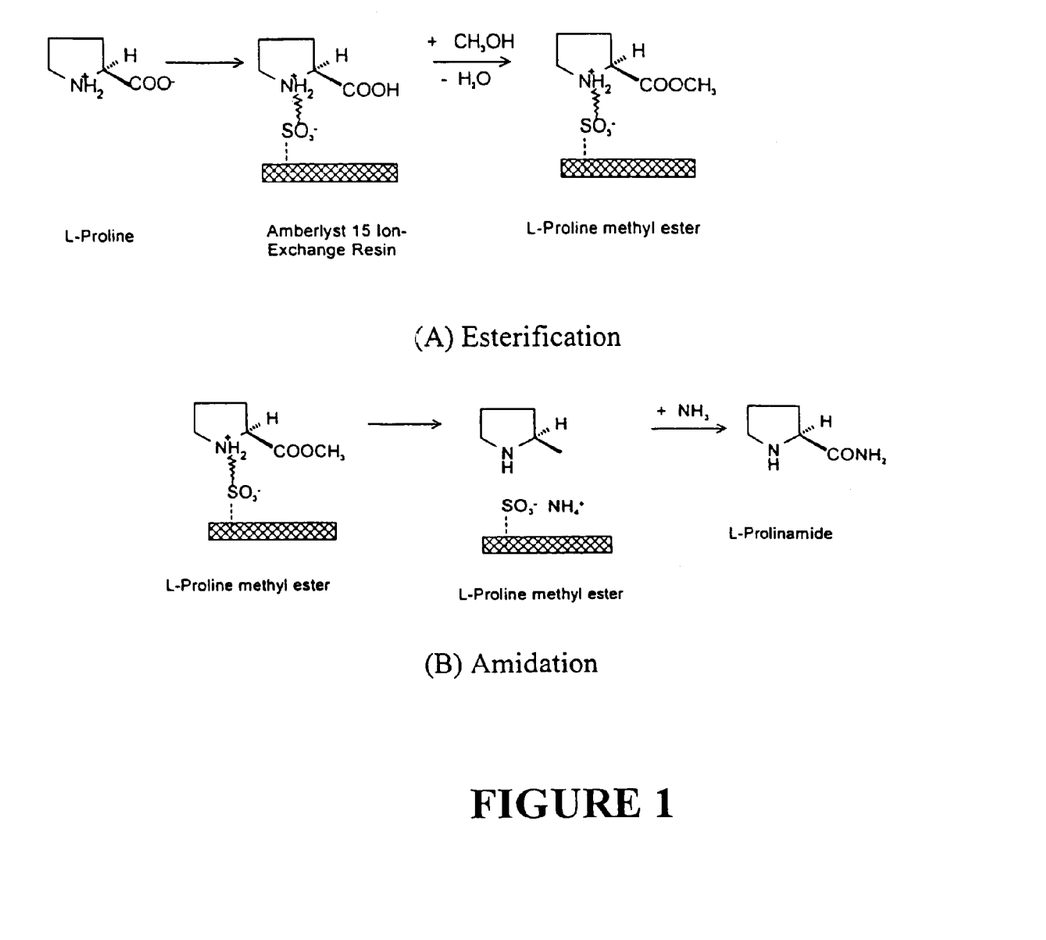
FIG. 1 is a reaction schematic that illustrates L-prolinamide synthesis using ion-exchange resins.

U.S. Pat. No. 4,017,513 describes resin-mediated (i.e., Dowex 50WX8 cation-exchange resin) synthesis of optically pure amino acid amides. These resin-based methods for amino acid amide synthesis comprise (a) esterification of an amino acid with methanol and (b) reaction of the ester with ammonia to form the amide (FIG. 1). Most amino acids are unreactive in polar solvents such as methanol because of zwitterion formation, but amino acid adsorption on a cation-exchange resin with, e.g., sulfonic acid groups, activates the amino acid molecules to esterification and subsequent amidation.

In the esterification reaction, the ion-exchange resin does not act as a catalyst because the ester remains adsorbed to the resin. Consequently, stoichiometric amounts of acid sites are required for complete amino acid esterification.

The process described in U.S. Pat. No. 4,017,513 is carried out in vessel containing an agitated slurry of resin particles with which the reactants are admixed. Ammonia is introduced as a vapor into the headspace of the reaction vessel, and is absorbed into the reaction slurry. Considerable resin attrition occurs in such a process due to the high agitation rates that are required to suspend the resin and contact it thoroughly with the reactants. Such agitation results in mechanical degradation of resin, i.e., the production of fine resin particles. The fine resin particles slow processing significantly because filtration of slurries containing fine solids is very slow. Further, fine particles are likely to increase the surface tension of the slurry and decrease the rate of ammonia absorption into the slurry, resulting in a slow amidation reaction. Thus, when practicing a process that requires filtration, either of final product or of some reaction intermediate, the production of fine particles should be avoided. Suspension of large amounts of dense resin particles with minimal attrition is particularly difficult in pilot-plant or production-scale reaction vessels. Thus, there is a need in the art for methods for the synthesis of amino acid amides using cation exchange resins which do not suffer from the problems associated with fine particle formation due to agitation of resin.

SUMMARY OF THE INVENTION

The present inventors have discovered a method for the synthesis of amino acid amides utilizing cation exchange resins that does not suffer from the problems associated with the filtration of cation exchange resin from reaction products and fine resin particle formation.

In one aspect, the invention relates to a method for the synthesis of amino acid amides which comprises providing a fixed bed of a cation exchange resin, admixing a primary alcohol and an amino acid in a reaction vessel in fluid communication with the fixed bed to form a first mixture, contacting the fixed bed of cation exchange resin with the first mixture for a period of time, thereby causing amino acid ester intermediate to be formed on the cation exchange resin, adding liquid ammonia to the reaction vessel, and contacting the fixed bed of cation exchange resin with ammonia, the fixed bed having previously been contacted with the first mixture.

In another aspect, the invention relates to a method for the synthesis of amino acid amides which comprises providing a fixed bed of a cation exchange resin, admixing a primary alcohol and an amino acid in a reaction vessel in fluid communication with the fixed bed to form a first mixture, contacting the fixed bed of cation exchange resin with the first mixture for a period of time, thereby causing amino acid ester intermediate to be formed on the cation exchange resin, adding liquid ammonia to the reaction vessel to form a second mixture, and contacting the fixed bed of cation exchange resin with second mixture, the fixed bed having previously been contacted with the first mixture, which further comprises contacting the fixed bed of cation exchange resin with the first mixture by recirculating the first mixture between the fixed bed and the reaction vessel for period of time sufficient for at least about 50% of the amino acid to be esterified. In another, preferred aspect, the method also comprises contacting the the fixed bed of cation exchange resin with the liquid ammonia-containing second mixture by recirculating the ammonia between the fixed bed and the reaction vessel for a sufficient period of time until at least about 75% of the amino acid ester intermediate is converted into amino acid amide.

In yet another, preferred, aspect of the method of the invention, the cation exchange resin employed in the method is a stirene-divinylbenzene-based sulfonic acid group-containing resin, and the ammonia to amino acid mole ratio is between about 11 and about 30.

In a particularly preferred embodiment, the invention relates to a method for the synthesis of L-prolinamide which comprises providing a fixed bed of a stirene-divinylbenzene-based sulfonic acid group-containing cation exchange resin, admixing methanol and L-proline in a reaction vessel in fluid communication with the fixed bed to form a first mixture, repeatedly contacting the fixed bed of stirene-divinylbenzene-based sulfonic acid group-containing cation exchange resin with the first mixture by recirculating the first mixture between the fixed bed and the reaction vessel for period of time sufficient for between about 60% and about 75% of the L-proline to be esterified to L-proline methyl ester intermediate on the resin, adding liquid ammonia to the reaction vessel to form a second mixture, where the ammonia to L-proline mole ratio is between about 11 and about 25, and repeatedly contacting the the fixed bed of cation exchange resin with the liquid ammonia-containing second mixture by recirculating the second mixture between the fixed bed and the reaction vessel for a sufficient period of time until at least about 95% of the L-proline methyl ester intermediate is converted into L-prolinamide.

DETAILED DESCRIPTION OF THE INVENTION

All patents, patent applications and publications cited herein are incorporated by reference in their entirety. In the case of a conflict in terminology, the present specification is controlling.

Definitions

As used herein, the term "cation exchange resin" refers to a solid composition that binds positively charged molecules, ions, or moieties when a solution containing such positively charged species are contacted with the composition. Typically, a cation exchange resin is a polymer that contains negatively charged functional groups. Suitable resins for the methods of the invention include any of the weak or strong cation exchange resins known by those of ordinary skill in the art. The resins can be made from any of the general types of polymers such as stirene, acrylic, phenolic, and the like, modified by having a carboxylic or sulfonic acid group attached thereto in the range to produce the required pKa range. They may be cross-linked to any degree, and preferably are in beaded form.

As used herein, the term "sulfonic acid group-containing resin" refers to a cation exchange resin where the negatively charged functional groups that impart the cation exchanging property to the resin are sulfonic acid groups.

As used herein, the term "stirene-divinylbenzene-based resin" refers to an ion exchange resin which comprises polymers of functionalized stirene-divinylbenzene. The functionalization imparts the ion-exchange properties to the resin.

As used herein, the term "primary alcohol" refers to any one of methyl, ethyl, propyl, butyl, pentyl, hexyl, heptyl, octyl, or nonyl alcohols.

As used herein, the term "liquid ammonia" refers to ammonia that is in the liquid phase due to its being subjected to high pressure, e.g., at 114 psig at room temperature.

As used herein, the term "recirculating" refers to a process whereby reaction mixture is caused to repeatedly flow into the fixed bed of cation exchange resin, out of the bed, into an agitated reaction vessel, out of the reaction vessel, and then into the fixed bed of cation exchange resin.

As used herein, the term "cooled" refers to a process whereby the temperature of a reaction mixture is decreased either by termination of application of heat or by contacting the reaction vessel containing the reaction mixture with a chilled solid or liquid. In general, cooling will reduce the temperature of a reaction mixture to between about 20 and 30° C., preferably to about 25° C.

As used herein, the term "mole ratio" refers to integer that results when dividing the number of moles of ammonia introduced into the reaction mixture of the invention by the number of moles of amino acid introduced into the reaction mixture.

Figure 2:
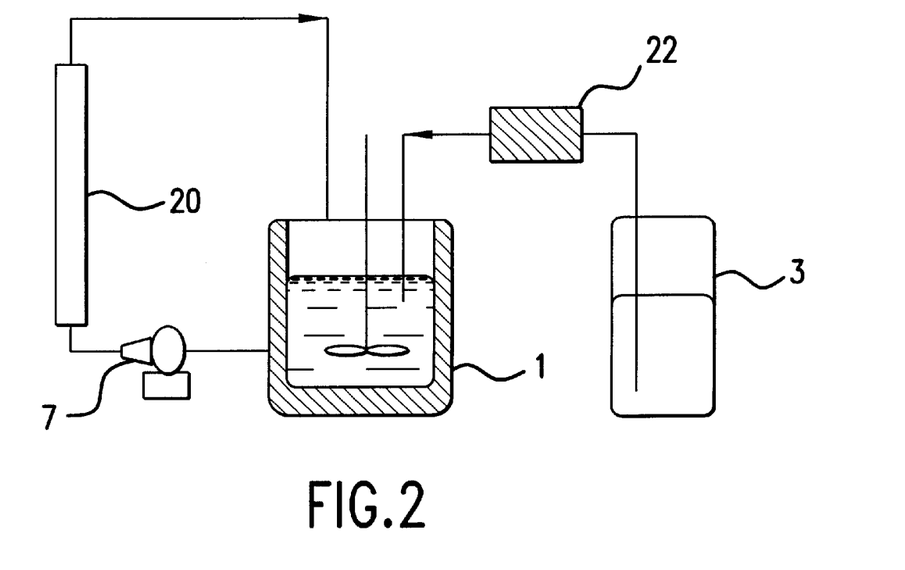
FIG. 2 is a simplified schematic diagram for an external recycle reactor for amino acid amide synthesis.
Figure 3:
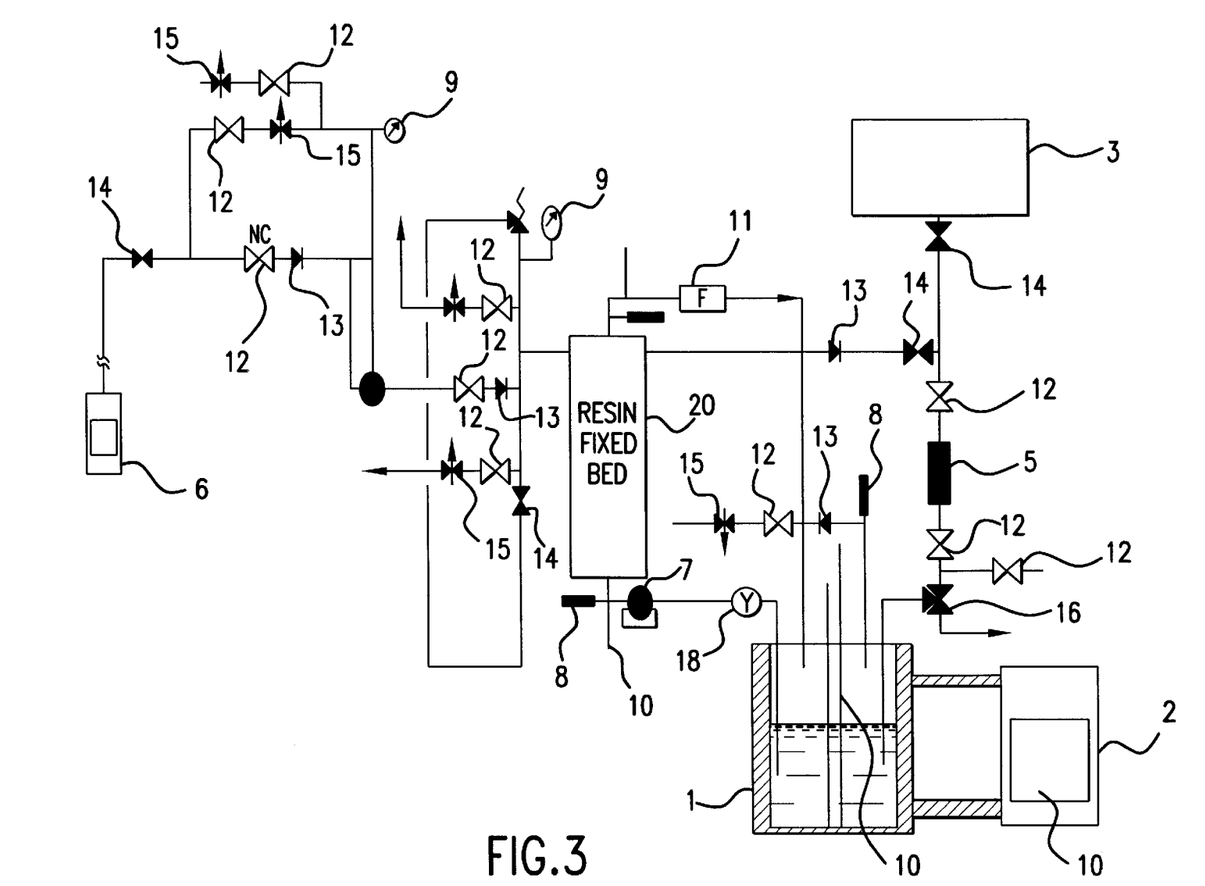
FIG. 3 is a detailed schematic diagram for an external recycle reactor for amino acid amide synthesis.

A simplified schematic diagram of an exemplary apparatus suitable for performing the methods of the invention is shown in FIG. 2. A more detailed diagram of such an apparatus is shown in FIG. 3. Referring to either of FIGS. 2 or 3, the container for the external fixed bed 20 can comprise, e.g., a tube, preferably a stainless steel tube, that is attached to a jacketed stirred vessel, e.g., one manufactured by Parr Instrument Co. using the appropriate tubing and fittings. Cation exchange resin particles are confined in the tube by wire screens that are fine enough to contain the cation exchange resin. If resin swelling is anticipated upon soaking in methanol, the tube length should be selected to allow for 100% resin swelling. The resin bed 20 is packed with a compressible packing material, e.g., glass wool, at either end to confine the initially unswelled resin in the bed. The packing material subsequently becomes compressed to accommodate the larger volume of swelled resin.

To monitor the pressure drop across the bed and temperature changes due to the esterification and amidation reactions, pressure transducers 8, pressure gauges 9, and temperature sensors 10 are installed at both ends of the bed. The outer tube wall is insulated, e.g., with silicon rubber, and may be jacketed to circulate a cooling liquid to obtain better heat transfer. The fluid in the external recycle reactor is circulated with a pump 7, e.g., an external gear pump. The recycle flow rate is measured using a flow meter 11, e.g., a turbine flow meter. The temperature and pressure in the agitated vessel are also monitored.

Dissolved ammonia in methanol flashes upon depressurizing. To make concentration measurements, it is necessary to sample the reaction mixture in order to perform, e.g., gas chromatographic ("GC") analysis under pressure. A specialized pressure-lock syringe (e.g., Micro-Flo™ from VICI Precision Sampling Inc., USA) should be used for proper sampling, with the adapter yoke 18 and the syringe guide used for sampling mounted between the pump 7 and the reactor vessel 1.

In a preferred embodiment, a liquid ammonia dosing system 22 is employed. A preferred dosing system comprises a liquid ammonia tank with a dip tube 3, a manual on-off valve 14, 2 air-actuated valves 12, a bomb 5, connecting tubing, and a manual three way valve 16. To observe ammonia flow, short Teflon™ tubing pieces (1") are employed at both ends of the bomb. The volume between the ammonia discharge valve and ammonia fill valve is determined. Controlled addition of ammonia to the reactor is achieved by filling the known volume between the two valves with ammonia, and discharging this volume into the reactor (see below). The periodic operation of the ammonia discharge valve and ammonia fill valve can be automated using appropriate valve control systems.

Figure 4:
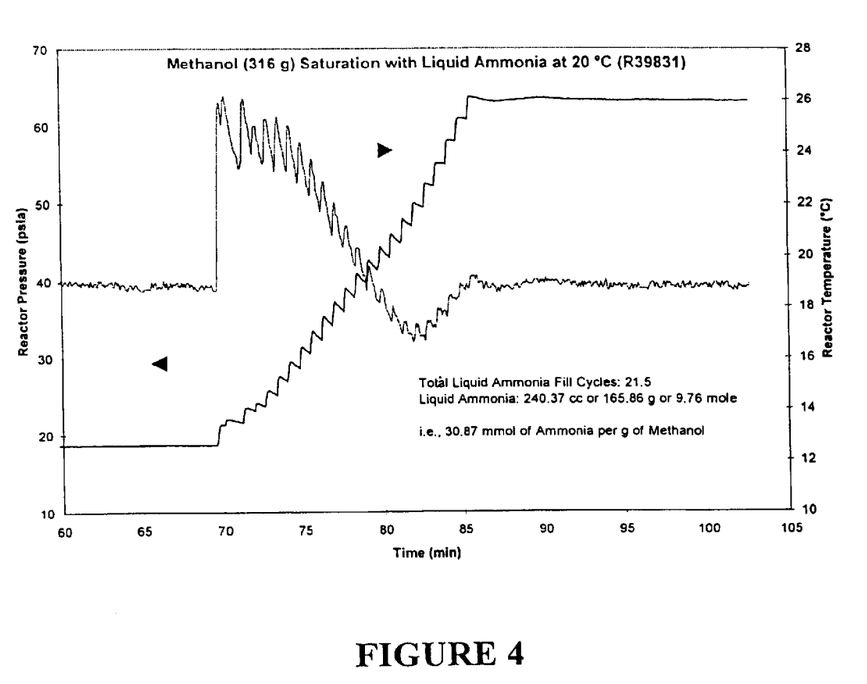
FIG. 4 is a graph demonstrating controlled dosing of liquid ammonia into methanol using an automated delivery system.

Before ammonia introduction into the reactor, the system is primed by opening the ammonia fill valve 12, waiting several seconds, closing the ammonia fill valve, opening the ammonia discharge valve 12, and then closing the latter. This cycle is repeated several times until the dosing system 22 is filled with liquid ammonia. After priming, ammonia is introduced into the reactor 1 using the number of fill/discharge cycles sufficient to give the reactor pressure necessary to give the desired $NH_3$ mole fraction in the liquid phase. The latter is estimated using known thermodynamic data (Kudo, S. and Toriumi, T., *Tohoku Daigaku Hisui Kagaku Kenkyusho Hokoku,* (1959), 8, 27, (b) Inomata, H., Ikawa, N., Arai, K., and Saito, S., *J. Chem. Eng. Data,* (1988), 33, 26) or correlations. The volume of liquid ammonia charged is thus calculated from the product of the volume between the ammonia fill valve and ammonia discharge valve and the number of fill/discharge cycles. An example of controlled liquid ammonia addition into 316 g of methanol at 20° C. is shown in FIG. 4. Generally, the amount of ammonia flashing into the vapor phase is calculated to be less than 0.5% of the mass of liquid added (i.e., essentially all of the liquid ammonia remains in the liquid phase). Thus, the ammonia concentration in the liquid phase can be estimated within 1% based on the amount dosed.

The fixed bed 20 is typically packed with a cation exchange resin. The agitated reaction vessel is charged with methanol. Methanol circulation to the fixed bed is initiated at about 20° C. and the resin is soaked for at least about 1 hour. Subsequently, the amino acid and more methanol are added, e.g., through an opening in the reactor headplate. The extra methanol is added to compensate for methanol loss due to holdup and absorption on the resin and thus maintain a constant volume in the reactor vessel. The reactor temperature is maintained between about 20 and about 65° C., preferably from between about 40 and about 65° C., e.g., at about 40, 50, or 60° C., using cooling fluid recirculating through a temperature controller bath 2. The resin-mediated esterification of the L-amino acid is carried out for about 10 to about 20 hours, preferably from about 12 to about 18 hours, most preferably for about 12 to 15 hours. This first reaction mixture is then cooled, preferably to about 25° C., in preparation for ammonia introduction into the recirculating fluid. Liquid ammonia is subsequently introduced into the reactor 1, forming a second reaction mixture and is recirculated through the fixed cation exchange resin bed 20 in admixture with the first reaction mixture. Liquid ammonia is recirculated in this way for from about 10 to about 30 hours, preferably from about 12 to about 18 hours. The mole ratio of ammonia to amino acid ester is from between about 10 and about 50, preferably between about 11 and about 30, most preferably between about 20 and 25. The temperature of the second, amidation reaction mixture is maintained at between about 20 and about 65° C., preferably between about 40 and about 60° C., e.g., at about 40, 50, or 60° C. Other components of the synthetic apparatus set out in FIG. 3 are a nitrogen cylinder 6 for purging the system, various pressure transducers 8, a flowmeter 11, various check valves 13, an adjustable needle valve 15, and a dome-loaded pressure regulator 17.

L-amino acid amide product isolation and purification, i.e., workup, generally includes distillation of the second reaction mixture between about 50 and about 70° C., preferably from about 58 to about 68° C., until about 80% of the methanol is removed. Subsequently, two volumes of toluene (relative to the distillation residue) are added to the concentrated dark brown reaction mixture, and distillation is continued until the distillate temperature reaches from between about 100 and about 110° C. This is followed by hot filtration at about 100° C. Solid yellow, uncharacterized residues are filtered using, e.g., a steam-jacket-heated Buchner funnel with Whatman filter paper (#1). The filtrate is stirred in, e.g., a round bottom flask equipped with a half-moon stirrer, and is cooled by natural air cooling. The product precipitates at temperatures between about 50° C. and 70° C. Once the temperature of the stirring suspension is below 50° C., n-heptane is added. After stirring the suspension at about 500 rpm for at least 1 hour at room temperature, the suspension is filtered through Whatman filter paper (#1) in a Buchner filter funnel to give an off-white wet cake which can be dried in a vacuum oven (at about, e.g., −26 inches Hg) at about 40° C. for at least 12 hours. The reaction progress can be monitored by GC analysis using, e.g., a Hewlett Packard 6890 GC system.

EXAMPLE 1

L-proline adsorbed on Amberlyst 15® cation exchange resin is converted to adsorbed methyl ester by refluxing in methanol for 2 hours at 65° C. The resin suspension is then filtered and washed with methanol in order to remove water formed during esterification to eliminate the possibility of amide hydrolysis. The ester-loaded resin is transferred to a reactor, and the amidation reaction is conducted in methanol by contacting the reaction mixture with dissolved ammonia, which is introduced in the headspace of the reactor vessel in the vapor phase. The amidation reaction under these conditions requires about 68 to 70 hours for complete ester conversion. The amide product in the liquid phase is recovered by filtering a resin/α-cellulose slurry. The product is purified by crystallization in toluene after methanol separation by distillation, with an overall yield of 66%.

EXAMPLE 2

The reaction according to Example 1 is performed but the resin filtration between the esterification step and the amidation step is eliminated. The amidation reaction time is shortened to about 20 hours. After filtering the resin, the final product yield is about 70%.

In the processes performed according to Examples 1 and 2, considerable resin attrition occurs during the reaction, as high impeller agitation rates are required to suspend the resin and contact it properly with the reaction mixture. The resin attrition results in slow filtration and may also impact resin esterification activity. A second problem is the energy inefficiency of ammonia gas introduction. Because ammonia is commercially available as a pressurized liquid in a cylinder, introduction of gaseous ammonia requires vaporization of the ammonia (which is energy intensive and difficult to control) followed by exothermic ammonia gas dissolution in the reaction mixture. Vaporizing large amounts of ammonia on a commercial scale would be particularly energy-intensive.

EXAMPLE 3

An alternative reactor configuration, an external recycle reactor, is used in a synthesis of L-prolinamide. In this configuration, the resin is placed in a fixed bed outside a jacketed stirred reaction vessel (FIGS. 2 and 3) and reaction mixture from the stirred reaction vessel is circulated through the fixed bed. The external fixed bed comprises a stainless-steel tube attached to a 1 liter jacketed stirred reaction vessel using appropriate fittings. 0.5 to 1 mm diameter resin particles are confined in the tube by fine wire screens. The fluid in the external recycle reactor is circulated with a gear pump. Liquid ammonia is added in 10 $cm^3$ volume increments. Good contacting is obtained between the reaction mixture and the resin particles without mechanical agitation and concomitant attrition of the resin particles. Because of minimal particle attrition, this configuration allows the recovery of substantially intact resin particles for regeneration. Liquid phase ammonia is pumped directly into the all-liquid first reaction mixture instead of introducing vapor phase ammonia into the headspace for subsequent absorption in directly into a resin slurry.

The fixed bed is packed with 81 g of Amberlyst 15® cation exchange resin, and the vessel is charged with 400 mL of methanol. With the agitator at 500 rpm, methanol circulation is initiated at 20° C. and 26 $cm^3$/s to soak the resin for 1 hour.

Addition of Amberlyst 15® resin to methanol at 20° C. is exothermic. Exotherms are observed in the bed upon resin soaking. With the methanol temperature at the bed inlet at 20° C., the exit temperature rises to 32° C. High bed temperatures can be prevented by initially contacting the resin using chilled methanol at <10° C.

Figure 5A:
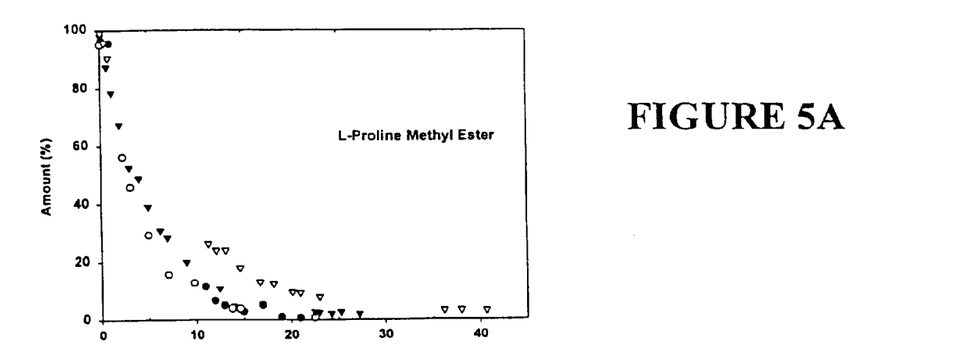
FIGS. 5A, 5B, and 5C are graphs illustrating the amidation of L-proline methyl ester with different ammonia concentrations in the second reaction mixture.
Figure 5B:
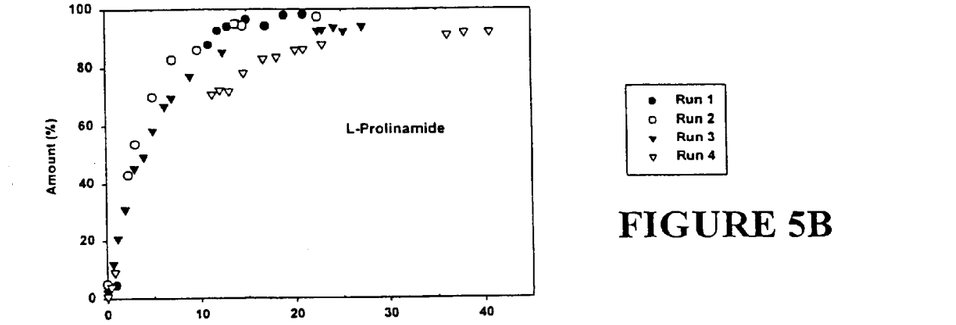
Figure 5C:
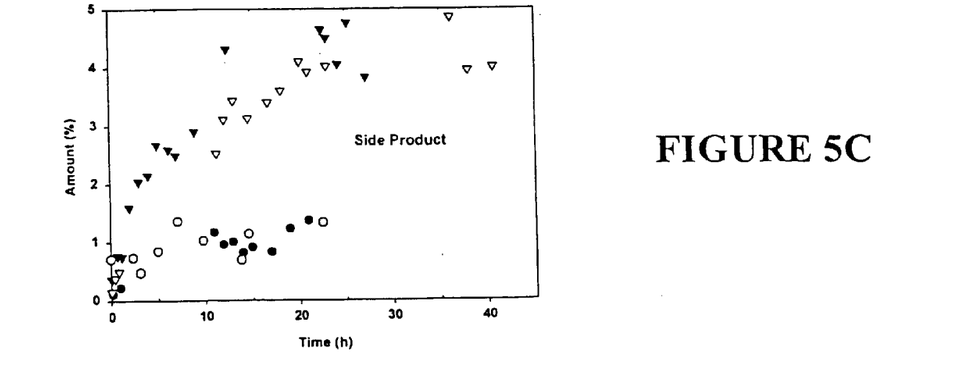

Subsequently, 30 g of L-proline and 200 mL of methanol are added to the agitated vessel through an opening in the reactor vessel headplate. The extra methanol is added to compensate for methanol loss due to holdup and adsorption on the resin and thus maintain an approximate 400 mL volume in the vessel. The vessel contents temperature is then raised to 65° C. over 0.5 hour, and the resin-mediated esterification of L-proline is carried out for 8 to 16 hours. After cooling to 25° C., liquid ammonia is added to the liquid in the agitated vessel while the reaction mixture recirculates. Approximately 95% conversion of L-proline methyl ester to L-prolinamide occurs over 12.7 hours when the first reaction mixture is saturated with liquid ammonia at 20° C. and 40 psig (Table 1, FIG. 5). The relationship between the amount of ammonia introduced and the amidation reaction time needed for high conversion and selectivity is quantified (Table 1, FIG. 5).

TABLE 1

| Run | NH$_3$/L-Proline | T (° C.) | P (psig) | Amt of NH$_3$ Relative to Run 1 (%) | Yield (%) | Reaction Time (h) |
|---|---|---|---|---|---|---|
| 1 | 50.63 | 20 | 40 | 100 | 75.16 | 12.7 |
| 2 | 24.44 | 40 | 21 | 48 | 68.84 | 12.8 |
| 3 | 11.35 | 60 | 21 | 22 | 60.4 | 17.4 |
| 4 | 6.98 | 60 | 18 | 14 | 64.3 | 27.6 |

*Determined by linear interpolation of the ester conversion vs. time data shown in FIG. 5.

GC analysis indicates that disappearance of L-proline in the first reaction mixture occurs in less than 2 hours after the circulation of the dissolved proline solution through the fixed bed. Esterification is continued for at least 10 more hours. The minimum esterification time is between about 4 and about 10 hours.

The temporal evolution of products as determined by GC is shown in FIG. 5 for the four runs listed in Table 1. Substantial L-proline methyl ester is present in the first reaction mixture when ammonia is introduced. Almost complete conversion of L-proline methyl ester to L-prolinamide occurs over about 21 hours, with saturation of the second reaction mixture with liquid ammonia at 20° C. and 40 psig. Another product, not identified, is detected in small amounts during amidation (FIG. 5).

Workup of the product includes an initial simple distillation of about 1000 g of the second reaction mixture between 58–63° C. until 800 g of methanol is removed. Subsequently, 400 mL of toluene is added to the concentrated dark brown reaction mixture, and the distillation is continued until the distillate temperature reaches 100 to 110° C., followed by hot filtration at about 100° C. A 2 liter, steam jacket-heated Buchner funnel with Whatman filter paper (#1) is used to filter solid yellow uncharacterized residues. The filtrate is stirred in a 2 liter round bottom flask equipped with a half-moon stirrer, and is cooled by natural air cooling. The product precipitates at temperatures between 50° C. and 70° C. Once the temperature of the stirring suspension is below 50° C., 150 mL of n-heptane is added. After stirring the suspension at 500 rpm for at least I hour at room temperature, the suspension is filtered through Whatman filter paper (#1) in a Buchner filter funnel to give an off-white wet cake which is dried in a vacuum oven (−26 in Hg) at 40° C. for more than 12 hours. The ion-exchange resin in the packed bed, following amidation, is washed twice by recirculating 400 mL of methanol through the resin bed. This washing results in recovery of some L-prolinamide, which is added to the final product before workup as described above.

The molar ratio of ammonia used to L-proline charged is very high (>50) in run 1, (Table 1). To reduce ammonia usage, the thermodynamic properties of the pure ammonia/methanol binary system is used to guide selection of amidation temperature and pressure. Thus, for a given reactor temperature, the desired ammonia liquid concentration could be selected by specification of the pressure.

To evaluate the impact of lower ammonia concentrations while still maintaining a reasonable reaction time, a two-fold lower ammonia concentration is used in run 2, but a higher amidation temperature (40 vs. 20° C.) is used, giving a saturation pressure of 21 psig. The amidation time, expressed as the time required to attain 95% ester conversion, is very similar (ca. 13 h) to the 20° C. run (Run 1, Table 1), so that the lower ammonia concentration is compensated for by an increase in the reaction temperature. Good selectivity is also obtained at in the 40° C. run, with approximately the same amount of side product formed.

An even lower ammonia concentration is used in run 3, corresponding to a NH$_3$/L-proline mole ratio of 11.4. A 60° C. amidation reaction temperature is selected, giving a 21 psig saturation pressure. Good conversion (>98%) and high selectivity (>95%) to L-prolinamide are obtained over 30 hours. However, the time for 95% ester conversion is higher (17.4 vs. 13 hours in the runs 1 and 2). Furthermore, by-product yield is almost three-fold higher. However, L-prolinamide yield is still high (see FIG. 5).

Further reduction of the liquid-phase ammonia concentration by 86% relative to the amount used in run 3, but keeping the reaction temperature at 60° C. (run 4), results in a considerably longer time for 95% ester conversion (28 hours vs. <20 hours). By-product yield is comparable to that obtained in run 3, where the ammonia concentration is lower by 78% relative to run 1.

Figure 6:
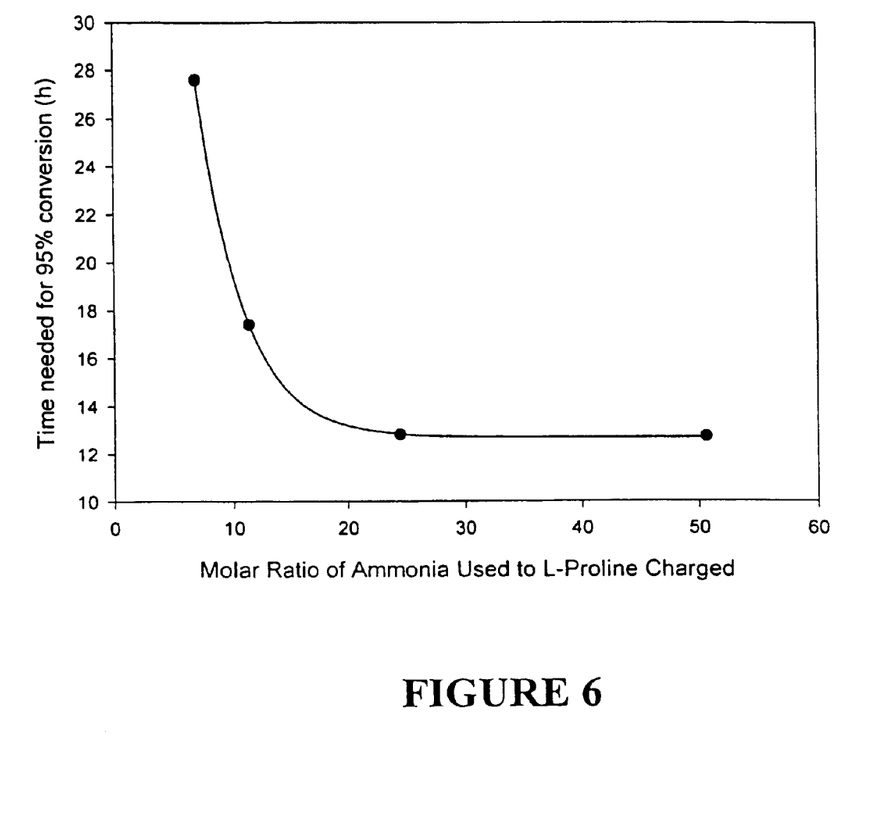
FIG. 6 demonstrates the relationship between amidation reaction time and ammonia amounts used.

The relationship between the NH$_3$/L-proline mole ratio and the corresponding 95% amidation reaction time is shown in FIG. 6, which indicates that the amidation reaction time changes sharply for NH$_3$/L-proline ratios below 11.

When the quantity of ammonia introduced approached the stoichiometric amount of acid sites on the resin, poor conversion and selectivity results. Approximately 0.381 moles of ammonia is required to titrate the acid sites on the resin. In a synthesis carried out at 60° C. (amidation temperature) in which 0.98 moles of ammonia were introduced (corresponding to a NH$_3$/L-proline mole ratio of 3.75), only 66% ester conversion is observed after 4 days with poor (50%) L-prolinamide selectivity.

What is claimed is:

1. A method for the synthesis of amino acid amides which comprises:
   providing a fixed bed of a cation exchange resin;
   admixing a primary alcohol and an amino acid in a reaction vessel in fluid communication with the fixed bed to form a first mixture;
   contacting the fixed bed of cation exchange resin with the first mixture for a period of time, thereby causing amino acid ester intermediate to be formed on the cation exchange resin;
   adding liquid ammonia to the reaction vessel to form a second mixture; and
   contacting the fixed bed of cation exchange resin with the second mixture, the fixed bed having previously been contacted with the first mixture.

2. The method of claim 1, which further comprises contacting the fixed bed of cation exchange resin with the first mixture by recirculating the first mixture between the fixed bed and the reaction vessel for period of time sufficient for at least about 50% of the amino acid to be esterified.

3. The method of claim 2, which further comprises contacting the the fixed bed of cation exchange resin with liquid ammonia by recirculating the second mixture between the fixed bed and the reaction vessel for a sufficient period of time until at least about 75% of the amino acid ester intermediate is converted into amino acid amide.

4. The method of claim 1, wherein subsequent to the admixing of the primary alcohol and the amino acid, the first mixture is heated in the reaction vessel to a temperature of between about 20 and about 65° C.

5. The method of claim 3, wherein prior to the adding of the ammonia, the first mixture is cooled.

6. The method of claim 1, wherein the primary alcohol is methanol.

7. The method of claim 1, wherein the amino acid is proline.

8. The method of claim 3, wherein the first mixture is recirculated for a sufficient period of time such that from at least about 60% to about 75% of the amino acid is converted into amino acid ester intermediate.

9. The method of claim 8, wherein the second mixture is recirculated for a sufficient period of time such that at least about 95% of the amino acid ester intermediate is converted into amino acid amide.

10. The method of claim 1, wherein the cation exchange resin is a sulfonic acid group-containing resin.

11. The method of claim 8, wherein the sulfonic acid group-containing resin is a stirene-divinylbenzene-based resin.

12. The method of claim 2 wherein the first mixture is recirculated from between about 12 to about 18 hours.

13. The method of claim 3 wherein the second mixture is recirculated from between about 12 and about 18 hours.

14. The method of claim 1 wherein the ammonia to amino acid mole ratio is between about 11 and about 30.

15. The method of claim 4 wherein subsequent to the addition of ammonia the second mixture is heated in the reaction vessel to a temperature of between about 40 and about 60° C.

16. The method of claim 3, wherein:
  the cation exchange resin is a stirene-divinylbenzene-based sulfonic acid group-containing resin;
  the primary alcohol is methanol;
  the amino acid is L-proline;
  the first mixture is recirculated for a sufficient period of time such that from at least about 60% to about 75% of the L-proline is converted into L-proline methyl ester intermediate;
  the second mixture is recirculated for a sufficient period of time such that at least about 95% of the L-proline methyl ester intermediate is converted into L-prolinamide; and
  the ammonia to amino acid mole ratio is between about 11 and about 25.

* * * * *

UNITED STATES PATENT AND TRADEMARK OFFICE
CERTIFICATE OF CORRECTION

PATENT NO. : 6,271,394 B1
DATED : August 7, 2001
INVENTOR(S) : Shekhar et al.

It is certified that error appears in the above-identified patent and that said Letters Patent is hereby corrected as shown below:

Drawings,
Sheet 3 of 6, Fig. 3, left side of drawing, blackend oval should have 17 pointing to it.

Column 2,
Lines 16 and 40, change "the the" to -- the --.
Lines 24, 28 and 32, change "stirene" to -- styrene --.

Column 3,
Lines 11, 20 and 22, change "stirene" to -- styrene --.
Line 13, change "pKa" to -- $pK_a$ --.

Column 7,
Line 45, change "I" to -- 1 --.

Column 9,
Line 18, change "stirene" to -- styrene --.

Column 10,
Line 8, change "stirene" to -- styrene --.

Signed and Sealed this

Tenth Day of September, 2002

Attest:

Attesting Officer

JAMES E. ROGAN
*Director of the United States Patent and Trademark Office*